United States Patent [19]

Couderc et al.

[11] Patent Number: 5,187,081
[45] Date of Patent: Feb. 16, 1993

[54] **PROCESS FOR PREPARING PROTEASE FROM *ENDOTHIA PARASITICA* USING GLUCANASES TO REDUCE VISCOSITY**

[75] Inventors: René Couderc, Castanet Tolosan; Bruno Eyssautier, Carentan; Martine Laporte, Ramonville Saint Agne; Marie-France Planard, Carentan, all of France

[73] Assignee: Sanofi, Paris, France

[21] Appl. No.: 311,776

[22] Filed: Feb. 17, 1989

[30] Foreign Application Priority Data

Feb. 18, 1988 [FR] France ................... 88 01934

[51] Int. Cl.$^5$ .................. C12N 9/58; C12N 21/00
[52] U.S. Cl. .................. 435/71.1; 435/223; 435/911
[58] Field of Search .................. 435/71.1, 223

[56] References Cited

U.S. PATENT DOCUMENTS 3,423,288  1/1969  Halleck et al. ............... 195/31

FOREIGN PATENT DOCUMENTS 1806986  7/1969  Fed. Rep. of Germany.
1401474  4/1965  France.
1179523  1/1970  United Kingdom.

OTHER PUBLICATIONS

Journal Officiel De La Republique Francaise, Mar. 20, 1981, International Milk Federation.
European Brewery Convention Proceedings of the 20th Congress, Helsinki 1985, pp. 419–425, IRL Press, Oxford, GB; J. Oksanen et al.: "Microbial Cellulase for Improving Filtrability of Wort and Beer".
P. Dupuy: "Utilisation Des Enzymes in Technologie Alimentaire", Use of Enzymes In Food Technology:, Symposium Int'l., Versailles, May 5–7, 1982, pp. 457–462.
Lavoisier, Paris, FR, J.-C. Villettaz et al.: "L'emploi des beta glucanases en oenologie".
Thomas et al., J. Agr. Food Chem 32:825–828(84).
Cereal Chemistry, vol. 63, No. 2, 1986, pp. 124–130, American Association of Cereal Chemists, Inc., St. Paul, Minn., US, K. M. Chung et al.: "Brewers condensed solubles. III. Enzymatic hydrolysis, viscosity reduction, and fermentation".
Erdelyi, A. et al., In Microbial associations and Interactions in food (1984) pp. 307–311.

*Primary Examiner*—Douglas W. Robinson
*Assistant Examiner*—S. Saucier
*Attorney, Agent, or Firm*—Foley & Lardner

[57] ABSTRACT

The present invention relates to a process for preparing protease from *Endothia parasitica*, wherein a glucanase or a mixture of glucanases acting on the viscosity increasing polysaccharides co-produced by the fungus, is introduced in the medium during or after fermentation.

7 Claims, No Drawings

PROCESS FOR PREPARING PROTEASE FROM *ENDOTHIA PARASITICA* USING GLUCANASES TO REDUCE VISCOSITY

The present invention relates to a process for preparing the protease which is secreted by *Endothia parasitica* and which coagulates the milk.

The preparation of this protease is already described in French Patent No. 1,401,474.

It has now been found that the viscosity of the fermentation medium increases considerably during the protease production stage, which complicates the operations of purification and isolation and more particularly ultrafiltration, and that the viscosity was particularly due to the presence of a polysaccharide co-produced by the microorganism together with protease.

The process according to the invention consists in introducing in the fermentation medium an enzyme which acts on the polysaccharide co-produced by the microorganism.

The enzyme may be introduced either at the beginning of the fermentation, or during the fermentation, or only during the final treatment of the fermentation medium, before filtration of the biomass or during concentration of the filtrate by ultrafiltration or microfiltration.

It is also possible to introduce different enzymes in the medium, either simultaneously or separately at different stages in the process.

Despite the presence of protease in the medium, the enzyme acts on the polysaccharide and reduces the viscosity of said medium, whether during the fermentation or after said fermentation was stopped.

In the process for preparing a coagulating protease by fermentation of *Endothia parasitica*, it is possible to use glucanases such as the beta-1,3 glucanase of Basidiomycetes described in U.S. Pat. No. 3,423,288, the beta-1,3 beta-1,6 glucanases, such as that marketed by NOVO under the trademark Glucanex or that marketed by Gist Brocades under the trademark Rapidase GL 150, or also fungal alpha-amylases, such as Fungamyl marketed by NOVO, or Amylase P200 marketed by Gist Brocades.

Generally, the enzyme will be introduced in the fermentation medium only after a culture period higher than 50% of the total duration estimated for a fermentation without enzyme, and preferably higher than 75%; under these conditions, the viscosity of the medium remains limited and the production of protease is not reduced and can even be improved; it is indeed found that the viscosity of the broth at the end of the operation is clearly less than that of a fermentation without enzyme, about 2 to 4 times less, without any reduction of the biomass.

The filtrate, which in this case is obtained after separation of the cells, is less viscous and can be concentrated by ultrafiltration in a conventional device up to a concentration higher than 30 g/l of protease and even up to 40 g/l, whereas after a conventional fermentation, the maximum concentration is only about 10 g/l; in the end, the final filtration on a low porosity membrane becomes easier.

According to another aspect, the process of the invention consists in treating the fermentation broths before filtration, for 1 to 5 hours, with 50 mg/l to 1 g/l of an enzyme composition active on the polysaccharide; the viscosity of the broth is reduced by 2 to 5 times as well as the filtering time required for separating the biomass from the medium containing the desired product.

According to a last aspect, the process of the invention consists in treating the filtrate obtained after separation of the cells, with an enzyme which hydrolyzes the polysaccharide co-produced during the concentration of this filtrate by ultrafiltration, in order to obtain a solution with a high concentration of the desired product when said product cannot be isolated directly by precipitation or evaporation of the solvent without being denaturated; in such a case, an alpha-amylase is preferably used.

The following is a description of examples of embodiment of the invention, applied to the fermentation of *Endothia parasitica.*

The inoculums are prepared from frozen spores of *Endothia parasitica*, strain ATCC 14729, by culture at 28° C. in a sterilized aqueous medium containing glucose, soya flour, mineral salts, and autolytic yeast extracts.

Production is carried out at 28° C. in a sterile aqueous medium of the same type as the previous one.

Viscosities are measured with a Brookfield viscometer; the coagulating activities were determined by the method recommended by the Fédération Internationale de Laiterie (International Milk Federation) and published in the Official Journal of the French Republic of Mar. 20, 1981.

EXAMPLE 1

Enzymatic Treatments During Fermentation

The tests were conducted with Glucanex or Amylase P 200 introduced at different moments of the fermentation, total duration of said fermentation being about 90 hours. Amylase P 200 contains a fungal alpha-amylase of *Aspergillus oryzae* and is in powder form, of FAU titer : 4540/g, one FAU corresponding to the quantity of enzyme hydrolyzing 5.26 g of soluble starch in one hour, at 37° C. and pH 4.7.

Glucanex is a powder containing an enzyme secreted by a Trichoderma strain; it contains 300 units of beta-glucanase per gramme.

The added quantities of enzyme, the addition times as well as the viscosity of the fermentation medium and the coagulating activity of the concentrate are indicated in Table I hereafter.

TABLE I

| TEST No | ENZYME | ENZYME CONCENTRATION (mg/l) | ADDITION TIME | VISCOSITIES OF MEDIUM (mPa.s) 40 hr | 47 hr | 64 hr | 72 hr | 88 hr | CONCENTRATE COAGULATING ACTIVITY g/l | CENTRATE VISCOSITY (mPa.s) |
|---|---|---|---|---|---|---|---|---|---|---|
| 1 | Glucanex | 20 | 0 | | | | 1000 | 1140 | 15 | |
| 2 | " | 20 | 42 | | | | 950 | 680 | 28 | |
| 3 | Control | 0 | | 1900 | 2600 | 3750 | 3700 | 2200 | 8.2 | 93 |
| 4 | Glucanex | 20 | 65 | 1900 | 2500 | 3050 | 1600 | 890 | 30 | 8 |
| 5 | " | 50 | 65 | | 2250 | 2700 | 750 | 420 | 41 | 9 |
| 6 | " | 100 | 65 | | 2250 | 2700 | 400 | 380 | 43 | 9 |

TABLE I-continued

| TEST No | ENZYME | ENZYME CONCENTRATION (mg/l) | ADDITION TIME | VISCOSITIES OF MEDIUM (mPa.s) | | | | | CONCENTRATE COAGULATING ACTIVITY g/l | CENTRATE VISCOSITY (mPa.s) |
|---|---|---|---|---|---|---|---|---|---|---|
| | | | | 40 hr | 47 hr | 64 hr | 72 hr | 88 hr | | |
| 7 | Control | 0 | | 1100 | 1700 | — | 1900 | 1000 | | |
| 8 | Glucanex | 10 | 45 and 68 | 950 | 1300 | — | 1100 | 650 | | |
| 9 | Control | 0 | | 720 | 920 | 640 | — | 800 | | |
| 10 | Glucanex | 200 | 23 | 240 | 240 | 106 | — | 400 | | |
| 11 | Amylase P200 | 20 | 45 and 65 | 1300 | 800 | 820 | 1000 | 850 | | |
| 12 | " | 40 | 65 | 1300 | 1250 | 1200 | 900 | | | |
| 13 | Control | 0 | 0 | 1500 | 1900 | 2200 | 2800 | 2100 | | |
| 14 | Glucanex | 42 | 72 | 1900 | 1800 | 1600 | 2700 | 900 | | |

The broths in tests 13 and 14 were treated after 90 hours of fermentation: filtration through canvas to separate mycelium, followed by concentration of the filtrate by ultrafiltration with a membrane permeable to compounds of molecular weight less than about 10000.

The results obtained are shown in Table II below.

Test 13 was conducted in the conventional way without adding any enzyme; in test 14, 40 mg of Glucanex were added per liter of broth after 72 hours of fermentation.

TABLE II

| TEST N° | BROTH VISCOSITY (mPa.s) | WEIGHT OF BROTH | FILTRATION TIME | WEIGHT OF MYCELIUM | FILTRATE VISCOSITY | CONCENTRATE COAGULATING ACTIVITY | CONCENTRATE VISCOSITY |
|---|---|---|---|---|---|---|---|
| 13 | 1600 | 158 kg | 24 min | 31 kg | 5 | 10 g/l | 120 mPa.s |
| 14 | 900 | 142 kg | 19 min | 30.5 kg | 4 | 38 g/l | 120 mPa.s |

EXAMPLE 2

Enzymatic Treatments of the Broth at End of Fermentation

The broths were treated after 88 hours of culture; they contained about 7.5 g/kg of polysaccharide and had a viscosity of 1000 mPa.s. 200 mg/l of various enzymatic compositions in powder form or 10 ml/l of liquid enzymatic compositions were added at this stage.

The results obtained for various contact times at room temperature are shown in Table III hereunder.

TABLE III

| ENZYMATIC COMPOSITION | SUPPLIER | ENZYMATIC ACTIVITY | BROTH VISCOSITY (mPa.s) after | | | |
|---|---|---|---|---|---|---|
| | | | 0.5 hr | 1 hr | 2 hr | 5 hr |
| Hemicellulase Reg 2 | Gist-Brocades | Pectinase + galactanase + galactomannase | 920 | 770 | 520 | 550 |
| Fungamyl | Novo | Alpha-amylase | 690 | 550 | 550 | 450 |
| Amylase P 200 | Gist-Brocades | Alpha-amylase | 850 | 600 | 680 | 550 |
| Glucanex | Novo | Beta-1,3 beta-1,6 glucanase | 650 | 420 | 280 | 150 |
| Rapidase GL 150 | Gist-Brocades | Beta-1,3 beta-1,6 glucanase | 850 | 600 | 520 | 480 |
| finizym | Novo | Beta-1,3 beta-1,4 glucanase | 920 | 900 | 880 | 850 |

EXAMPLE 3

Enzymatic Treatments of the Fermentation Filtrate after Separation of the Mycelium The enzyme was added before the beginning of the ultrafiltration. Fungamyl is a liquid composition of fungal alpha-amylase of titer 800 FAU/g; Maxamyl and BAIF, marketed by Gist-Brocades, are bacterial amylases.

The Table IV shows the drop of viscosity with time of a pre-concentrated filtrate in which various enzymes have been introduced in variable quantities.

The filtrate, preconcentrated by ultrafiltration, and having a pH of 4.3, had a viscosity of 70 mPa.s; the quantities of enzymatic compositions are given in g for 100 g of protease in the preconcentrated filtrate.

TABLE IV

| ENZYMATIC COMPOSITION | QUANTITY g/100 g | VISCOSITY (mPa.s) after | | | | |
|---|---|---|---|---|---|---|
| | | 25 mins. | 50 mins. | 100 mins. | 150 mins. | 175 mins. |
| Maxamyl | 4.76 | 58 | 46 | 38 | 32 | |
| BAIF | 3.8 | 46 | 32 | 26 | 24 | |
| Amylase P200 | 4.76 | 5 | 5 | 5 | 5 | 5 |
| | 0.95 | 7.5 | 5 | 5 | 5 | 5 |
| | 0.095 | 22 | 18 | 16 | 15 | 14 |
| Fungamyl | 4.76 | 10 | 10 | 10 | | |
| | 0.095 | 28 | 20 | 16 | | |
| Glucanex | 0.95 | 63 | 62 | 63 | 62 | |
| Dextranase Novo | 4.76 | 70 | 68 | | 65 | |
| Pectinase SP 249 Novo | 4.76 | 70 | 68 | | 65 | |

EXAMPLE 4

Enzymatic treatments during concentration of the filtrate

The whole process was carried out in the conventional way: fermentation, separation of the biomass by filtration and concentration of the filtrate by ultrafiltration.

This last operation was discontinued when the flow had become virtually nil. The concentrate was then found to be of pH 3.9 and to contain 9 g/l of protease.

40 mg of amylase P 200 or 40 mg of Fungamyl were introduced for 10 kg of concentrate and ultrafiltration was resumed after leaving the mixtures to stand for 2 hours and 15 minutes at room temperature.

After 45 minutes of concentration, the concentrate obtained had a protease concentration of 45 g/l in the case of the treatment with amylase P 200, and 42 g/l in the case of the treatment with Fungamyl.

What is claimed is:

1. In a process for preparing a protease, comprising the steps of culturing the fungus *Endothia parasitica* in a suitable fermentation medium, separating the cells from the medium, concentrating the resultant medium, and isolating from the concentrated medium a protease produced by the fungus, the improvement comprising reducing increased viscosity caused by a polysaccharide or polysaccharides produced by *Endothia parasitica* during the fermentation process by adding to said medium an enzyme selected from the group consisting of a beta-1,3 glucanase, a beta-1,3-beta-1,6 glucanase or an alpha-amylase, or a mixture thereof wherein said enzyme or mixture of enzymes is introduced during or after fermentation, but prior to isolation of said protease.

2. A process as claimed in claim 1, wherein said enzyme or mixture of enzymes is introduced into said medium during fermentation.

3. A process as claimed in claim 1, wherein said enzyme or mixture of enzymes is introduced into said medium at the end of fermentation but before the separation of the cells.

4. A process as claimed in claim 1, wherein said enzyme or mixture of enzymes is introduced into said medium after the separation of the cells but before concentration of the medium by ultrafiltration or microfiltration.

5. A process as claimed in claim 1 wherein said enzyme or mixture of enzymes is introduced into said medium during concentration by ultra-filtration.

6. A process as claimed in claim 1, wherein said enzyme is a beta-1,3 beta-1,6 glucanase, which is introduced into said medium during or at the end of fermentation.

7. A process as claimed in claim 1 wherein said enzyme is an alpha-amylase and said alpha-amylase is introduced into said medium during concentration.

* * * * *